United States Patent [19]

Rose et al.

[11] Patent Number: 5,595,891
[45] Date of Patent: Jan. 21, 1997

[54] METHOD FOR PRODUCING A POLYNUCLEOTIDE FOR USE IN SINGLE PRIMER AMPLIFICATION

[75] Inventors: Samuel Rose; Linda M. Western, both of Mountain View; Martin Becker, Palo Alto; Edwin F. Ullman, Atherton, all of Calif.

[73] Assignee: Behringwerke AG, Marburg, Germany

[21] Appl. No.: 555,323

[22] Filed: Jul. 19, 1990

[51] Int. Cl.⁶ .............................. C12P 19/34; C12Q 1/68
[52] U.S. Cl. ................. 435/91.5; 435/6; 935/77; 935/78
[58] Field of Search .................. 435/6, 91, 91.1; 935/77, 78; 536/27

[56] References Cited

U.S. PATENT DOCUMENTS

| | | | |
|---|---|---|---|
| 4,683,195 | 7/1987 | Mullis et al. | 435/6 |
| 5,066,584 | 11/1991 | Gyllensten et al. | 435/91 |
| 5,508,178 | 4/1996 | Rose et al. | 435/91.1 |

FOREIGN PATENT DOCUMENTS

| | | | |
|---|---|---|---|
| 224995 | 6/1987 | European Pat. Off. | 435/6 |
| 379369 | 7/1990 | European Pat. Off. | 435/6 |
| WO90/11374 | 11/1990 | WIPO | 435/6 |

OTHER PUBLICATIONS

Frohman et al., PNAS(USA)85:8998–9002 (Dec. 1988).
Gullensten et al., PNAS(USA)85:7652–7656 (Oct. 1988).
Nelson et al., PNAS(USA)86:6686–6690 (Sep. 1989).

*Primary Examiner*—Stephanie W. Zitomer
*Attorney, Agent, or Firm*—Theodore J. Leitereg

[57] ABSTRACT

A method is disclosed for producing a single stranded polydeoxynucleotide having two segments that are non-contiguous and complementary with each other. The method comprises the steps of providing in combination (1) a polynucleotide having two non-contiguous, non-complementary nucleotide sequences S1 and S2 wherein S2 is 5' of S1 and is at least ten deoxynucleotides long and (2) an extender probe comprised of two deoxynucleotide sequences, wherein the sequence at the 3'-end of the extender probe is hybridizable with S1 and the other of the deoxynucleotide sequences is homologous to S2 and (b) extending the extender probe along the polynucleotide. The method can also comprise providing in the combination a polydoxynucleotide primer capable of hybridizing at least at its 3'-end with a nucleotide sequence complementary to S2 under conditions where (1) the extended extender probe is rendered single stranded, (2) the polydeoxynucleotide primer hybridizes with and is extended along the extended extender probe to form a duplex comprising extended primer, (3) the extended primer is dissociated from the duplex, and (4) the primer hybridizes with and is extended along the extended primer to form a duplex comprising extended primer, and repeating steps (3) and (4). The method finds particular application in the detection of polynucleotide analytes.

49 Claims, 2 Drawing Sheets

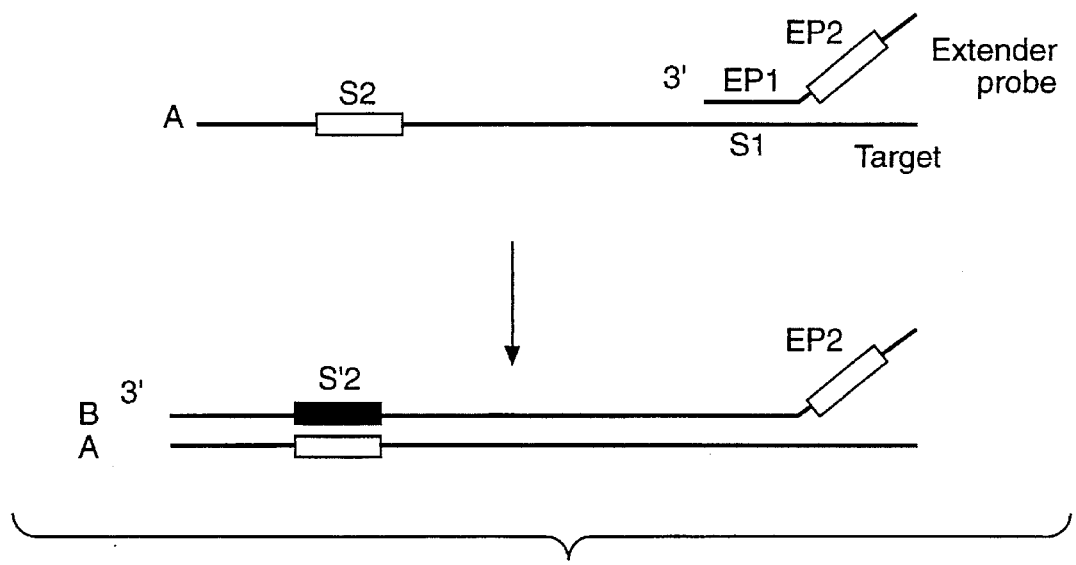
FIG._1
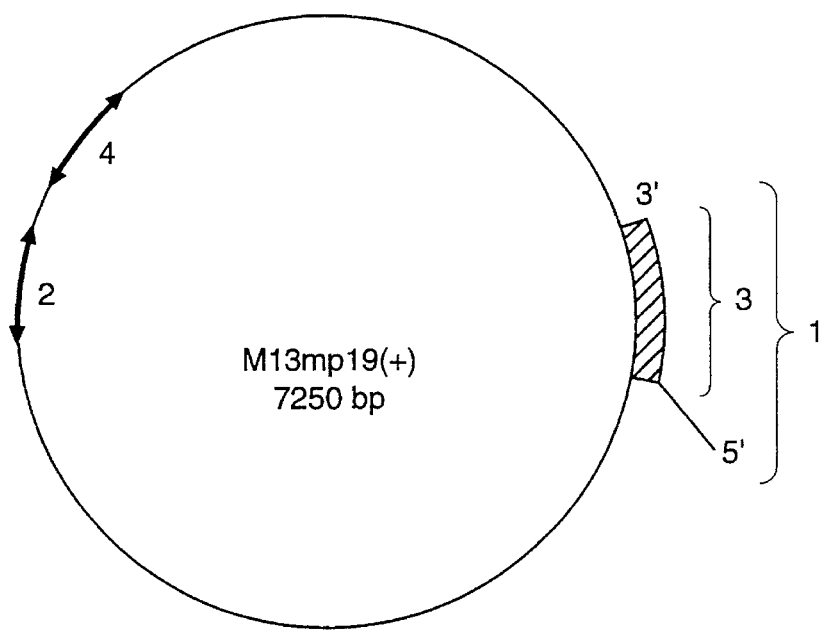
FIG._3

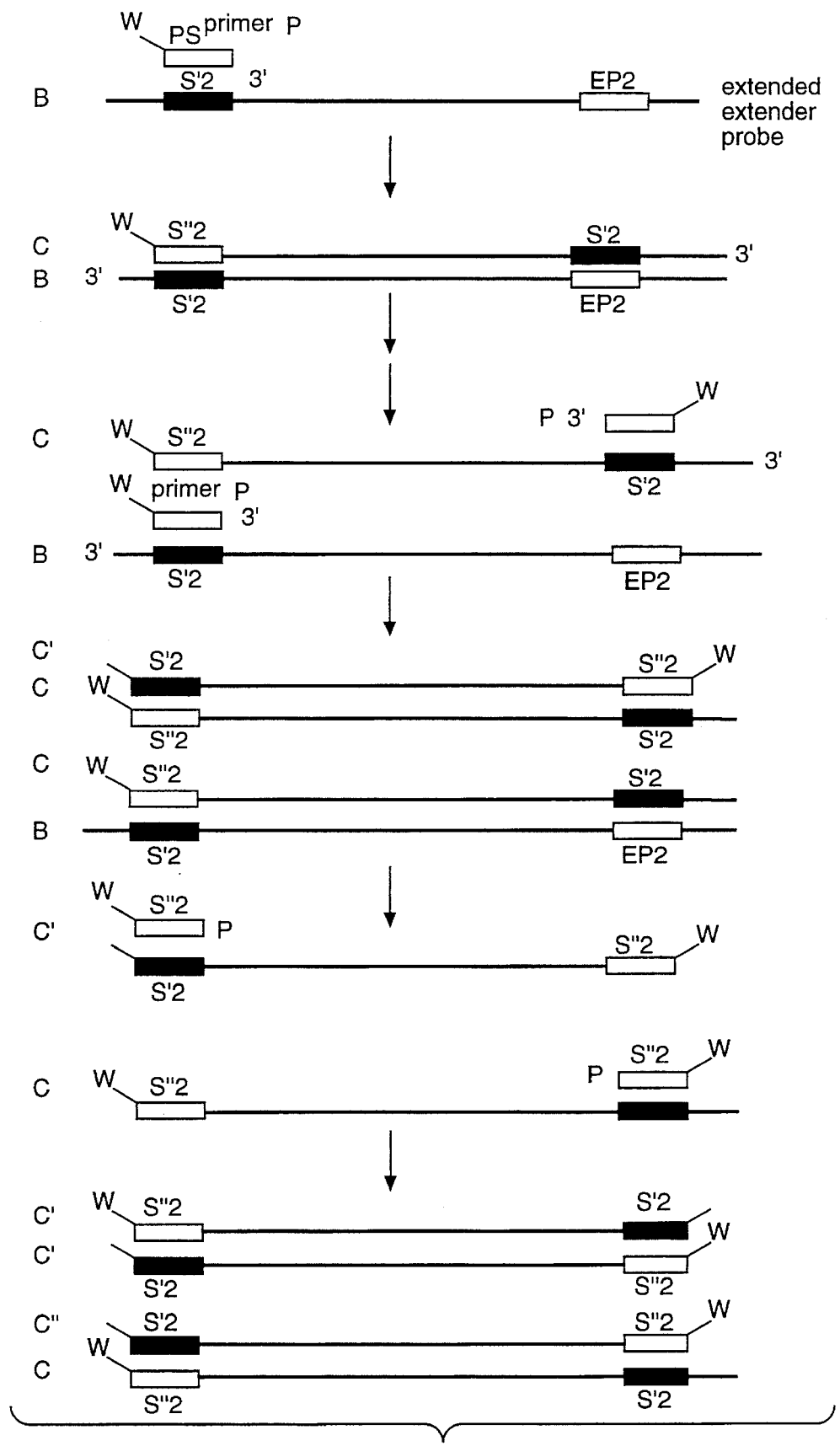
FIG._2

METHOD FOR PRODUCING A POLYNUCLEOTIDE FOR USE IN SINGLE PRIMER AMPLIFICATION

BACKGROUND OF THE INVENTION

1. Field of the Invention

Nucleic acid hybridization has been employed for investigating the identity and establishing the presence of nucleic acids. Hybridization is based on complementary base pairing. When complementary single stranded nucleic acids are incubated together, the complementary base sequences pair to form double stranded hybrid molecules. The ability of single stranded deoxyribonucleic acid (ssDNA) or ribonucleic acid (RNA) to form a hydrogen bonded structure with a complementary nucleic acid sequence has been employed as an analytical tool in molecular biology research. The availability of radioactive nucleoside triphosphates of high specific activity and the $^{32}P$ labelling of DNA with T4 kinase has made it possible to identify, isolate, and characterize various nucleic acid sequences of biological interest. Nucleic acid hybridization has great potential in diagnosing disease states associated with unique nucleic acid sequences. These unique nucleic acid sequences may result from genetic or environmental change in DNA by insertions, deletions, point mutations, or by acquiring foreign DNA or RNA by means of infection by bacteria, molds, fungi, and viruses. Nucleic acid hybridization has, until now, been employed primarily in academic and industrial molecular biology laboratories. The application of nucleic acid hybridization as a diagnostic tool in clinical medicine is limited because of the frequently very low concentrations of disease related DNA or RNA present in a patient's body fluid and the unavailability of a sufficiently sensitive method of nucleic acid hybridization analysis.

Current methods for detecting specific nucleic acid sequences generally involve immobilization of the target nucleic acid on a solid support such as nitrocellulose paper, cellulose paper, diazotized paper, or a nylon membrane. After the target nucleic acid is fixed on the support, the support is contacted with a suitably labelled probe nucleic acid for about two to forty-eight hours. After the above time period, the solid support is washed several times at a controlled temperature to remove unhybridized probe. The support is then dried and the hybridized material is detected by autoradiography or by spectrometric methods.

When very low concentrations must be detected, the current methods are slow and labor intensive, and nonisotopic labels that are less readily detected than radiolabels are frequently not suitable. A method for increasing the sensitivity to permit the use of simple, rapid, nonisotopic, homogeneous or heterogeneous methods for detecting nucleic acid sequences is therefore desirable.

Recently, a method for the enzymatic amplification of specific segments of DNA known as the polymerase chain reaction (PCR) method has been described. This in vitro amplification procedure is based on repeated cycles of denaturation, oligonucleotide primer annealing, and primer extension by thermophilic polymerase, resulting in the exponential increase in copies of the region flanked by the primers. The PCR primers, which anneal to opposite strands of the DNA, are positioned so that the polymerase catalyzed extension product of one primer can serve as a template strand for the other, leading to the accumulation of a discrete fragment whose length is defined by the distance between the 5' ends of the oligonucleotide primers.

2. Description of the Prior Art

A process for amplifying, detecting and/or cloning nucleic acid sequences is disclosed in U.S. Pat. Nos. 4,683,195 and 4,683,202. Sequence polymerization by polymerase chain reaction is described by Saiki, et al., (1986) *Science*, 230: 1350–1354. A method of making an oligonucleotide is described in European Patent Application No. 0194545 A2. Belgian Patent Application No. BE 904402 discloses a mold for making DNA detection probes. Gene amplification in eukaryotic cells is disclosed in U.S. Pat. No. 4,656,134.

Langer, et al., *Proc. Natl. Acad. Sci. USA*, (1981) 78:6633–6637 discloses the enzymatic synthesis of biotin labelled polynucleotides and the use of these materials as novel nucleic acid affinity probes. The detection of vital genomes in cultured cells and paraffin imbedded tissue sections using biotin labelled hybridization probes is discussed by Brigati, et al., *Virology*, (1983) 126: 32–50. U.S. Pat. No. 4,486,539 discloses the detection of microbial nucleic acids by a one step sandwich hybridization test. Sensitive tests for malignancies based on DNA detection is described in U.S. Pat. No. 4,490,472. U.S. Pat. No. 4,480,040 discloses the sensitive and rapid diagnosis of plant viroid diseases and viruses employing radioactively labelled DNA that is complementary to the viroid or to the nucleic acid of the virus being diagnosed. European patent application 83106112.2 (Priority U.S. patent application Ser. No. 391,440 filed Jun. 23, 1982) teaches modified labelled nucleotides and polynucleotides and methods of preparing, utilizing, and detecting the same. Methods and compositions for the detection and determination of cellular DNA are disclosed in U.S. Pat. No. 4,423,153. Specific DNA probes in diagnostic microbiology are discussed in U.S. Pat. No. 4,358,535. A method for detection of polymorphic restriction sites and nucleic acid sequences is discussed in European Patent Application No. 0164054 A1. U.S. Pat. No. 4,663,283 describes a method of altering double-stranded DNA.

Genomic amplification with transcript sequencing is discussed by Stoflet, et al., *Science* (1988) 239:491. Primer-directed enzymatic amplification of DNA with a thermostable DNA polymerase is described by Saiki, et al., *Science* (1988) 239:487. U.S. Pat. No. 4,724,202 discloses the use of non-hybridizable nucleic acids for the detection of nucleic acid hybridization. Bugawan, et al. *Biotechnology* (1988), 6: 943–947, describe the use of non-radioactive oligonucleotide probes to analyze enzymatically amplified DNA for prenatal diagnosis and forensic HLA typing.

Detection and isolation of homologous, repeated and amplified nucleic acid sequences is disclosed in U.S. Pat. No. 4,675,283. A single stranded self-hybridizing nucleic acid probe capable of repeatedly hybridizing to itself or other nucleic acids to form an amplified entity is described in U.S. patent application Ser. No. 888,058, filed Jul. 22, 1986. U.S. Pat. Nos. 4,683,195 and 4,683,202 disclose a homogeneous polynucleotide displacement assay with digestion of the displaced RNA single strand polynucleotide from the reagent complex and amplifying nucleic acid sequences with treatment of separate complementary strands of the nucleic acid with two oligonucleotide primers. European Patent Application No. 0200362 describes a process for amplifying, detecting or cloning nucleic acid sequences and useful in disease diagnosis and in preparation of transformation vectors. A method for simple analysis of relative nucleic acid levels in multiple small samples by cytoplasmic dot hybridization is described in U.S. Pat. No. 4,677,054. A hybridization method of detecting nucleic acid sequences with a probe containing a thionucleotide is described in U.S. Pat. No. 4,647,529.

A simple and efficient enzymatic method for covalent attachment of DNA to cellulose and its application for hybridization-restriction analysis and for in vitro synthesis of DNA probes is described in *Nucleic Acids Research* (1986) 14:9171–9191. Cleavage of single stranded oligonucleotides by Eco RI restriction endonuclease is described in Nucleic Acid Research (1987) 12.: 709-716.

Exponential Amplification of Recombinant-RNA Hybridization Probes is described by Lizardi, et al., (1988) Bio/Technology 6:1197–1202. Fahrlander, et al., discusses Amplifying DNA Probe Signals: A Christmas Tree Approach in *Bio/Technology* (1988) 6:1165-1168.

A nucleic acid hybridization assay employing probes cross-linkable to target sequences is described in U.S. Pat. No. 4,599,303. The method involves the preparation of a specific single stranded ribonucleic acid or deoxyribonucleic acid molecule into which a bifunctional cross-linking molecule has been covalently incorporated. The incorporation is such that the cross-linking molecule retains the capacity to undergo a second reaction with the nucleic acid of the bacterial, vital, or mammalian chromosome, which is the target for the probe such as to form a covalent cross link. Following cross-linking, the uncrossed link probe is separated from covalently cross-linked probe-target complex using one of several procedures which differentiate between single stranded probe and double stranded covalently linked probe-target complex.

A hybridization method and probe for detecting nucleic acid sequences is described in U.S. Pat. No. 4,908,307. An amplified hybridization assay is described in U.S. Pat. No. 4,882,269 wherein a family of signal-generating secondary probes bind to a primary probe that hybridizes to the target sequence of interest.

Detection of target sequences in nucleic acids by hybridization using diagnostic and contiguous probes for diagnosis of genetic abnormality diseases, especially in an automated procedure, is described in European Patent Application No. 0 185 494A2. In the method a sample is hybridized with a probe complementary to a diagnostic portion of the target sequence (the diagnostic probe) and with a probe complementary to a nucleotide sequence contiguous with the diagnostic portion (the contiguous probe) under conditions wherein the diagnostic probe remains bound substantially only to the sample nucleic acid containing the target sequence. The diagnostic probe and contiguous probe are then covalently attached to yield a target probe that is complementary to the target sequence and the probes which are not attached are removed. In a preferred mode, one of the probes is labeled so that the presence or absence of the target sequence can then be tested by melting the sample nucleic acid target probe duplex, eluting the dissociated target probe, and testing for the label.

The above method suffers at least one disadvantage in that contiguous sequences are required. To carry out the method, one must identify the diagnostic sequence and the contiguous sequence and create diagnostic and contiguous probes complementary to the above sequences. If the diagnostic and contiguous sequences are not identified precisely, then the diagnostic and contiguous probes may not hybridize sufficiently and the assay specificity and sensitivity can be lost or substantially decreased.

A DNA amplification and subtraction technique is described in WO89/12695. The method involves isolating genomic or RNA-derived duplex fragments which are unique to one of two fragment mixtures. The fragments in positive-source and negative-source mixtures are separately equipped with end linkers, and each mixture is amplified by successive primed-strand replications, using a single primer which is homologous to the associated linker. The second source linker is biotinylated, and the fragments in this mixture are hybridized in molar excess with the fragments in the positive source mixture. DNA species which are not hybridized with the biotinylated species, i.e., species that are unique to the positive source mixture, are isolated after removal of hybridized species by affinity chromatography. Also disclosed is a method of amplifying a mixture of DNA fragments by repeated linker/primer replication.

U.S. patent applications Ser. Nos. 07/299,282 and 07/399,795, filed Jan. 19, 1989, and Aug. 29, 1989, respectively, describe nucleic acid amplification using a single polynucleotide primer. The disclosures of these two applications are incorporated herein by reference.

SUMMARY OF THE INVENTION

The invention disclosed herein includes methods and reagents for forming a single stranded polydeoxynucleotide having two segments that are non-contiguous and complementary with each other. The method finds particular application, for example, in single primer amplification assays.

In one embodiment of the invention a single stranded polydeoxynucleotide having two segments that are non-contiguous and complementary with each other is produced. The method of production comprises the steps of (a) providing in combination a polynucleotide having two non-contiguous, non-complementary nucleotide sequences, S1 and S2, wherein S2 is 5' of S1 and is at least ten nucleotides long and an extender probe comprised of two deoxynucleotide sequences, wherein the sequence at the 3' end of the extender probe is hybridizable with S1 and the other of the deoxynucleotide sequences is homologous to S2 and (b) extending the extender probe along the polynucleotide.

Another embodiment of the present invention involves a method for producing multiple copies of a single stranded polydeoxynucleotide having two segments that are non-contiguous and complementary with each other. The method comprises the step of providing in combination, either concomitantly or wholly or partially sequentially, (1) a polynucleotide having two non-contiguous, non-complementary nucleotide sequences, S1 and S2, wherein S2 is 5' of S1 and is at least ten nucleotides long, (2) an extender probe comprised of two deoxynucleotide sequences, wherein the sequence at the 3'-end of the extender probe is hybridizable with S1 and the other of the nucleotide sequences is homologous to S2 and not complementary to the polynucleotide, (3) a polydeoxynucleotide primer capable of hybridizing at least at its 3'-end with a nucleotide sequence complementary to S2, (4) DNA polymerase, and (5) deoxynucleoside triphosphates under conditions where (a) the extender probe is extended along the polynucleotide to form a duplex, (b) the extended extender probe is dissociated from the duplex, (c) the polydeoxynucleotide primer hybridizes with and is extended along the extended extender probe to form a second duplex comprising extended primer (d) the extended primer is dissociated from the second duplex, and (e) the primer hybridizes with and is extended along the extended primer to form a duplex comprising extended primer, and steps (d) and (e) are repeated.

In another embodiment the presence of a target nucleotide sequence in a medium suspected of containing the target nucleotide sequence is detected. The target nucleotide sequence has two non-contiguous, non-hybridizable nucleotide sequences, S1 and S2, wherein S2 is 5' of S1 and at least 10 nucleotides long. The method comprises the steps of:

(a) providing in combination, either concomitantly or wholly or partially sequentially, the medium, an extender probe having two deoxynucleotide sequences wherein the sequence at the 3'-end of the extender probe is hybridizable with S1 and the other of the deoxynucleotide sequences is homologous to S2 and not complementary to the target nucleotide sequence, a polydeoxynucleotide primer capable of hybridizing with a nucleotide sequence complementary to S2, DNA polymerase and deoxynucleoside triphosphates under conditions wherein (1) the extender probe is extended along the polynucleotide to form a duplex, (2) the extended extender probe is dissociated from the duplex, (3) the primer hybridizes with and is extended along the extended extender probe to form a second duplex comprising extended primer, (4) the extended primer is dissociated from the duplex, and (5) the primer hybridizes with and is extended along the extended primer to form a duplex comprising extended primer and steps (4) and (5) are repeated, and (b) examining for the presence of the extended primer.

Another embodiment of the invention involves a method for detecting the presence of a polynucleotide analyte in a sample suspected of containing the polynucleotide analyte. The method comprises the steps of:

(a) treating a medium containing the sample to form a single stranded target nucleotide sequence from the polynucleotide analyte, if present, the target nucleotide sequence having two non-contiguous, non-complementary nucleotide sequences, S1 and S2, wherein S2 is 5' of S1, and is at least ten nucleotides long, (b) combining the medium with an extender probe having two polydeoxynucleotide sequences wherein the sequence at the 3'-end of the extender probe is hybridizable with S1 and the other of the deoxynucleotide sequence is homologous to S2 and not complementary to the target sequence, a polydeoxynucleotide primer capable of hybridizing with a nucleotide sequence complementary to S2, deoxynucleoside triphosphates, and DNA template dependent polydeoxynucleotide polymerase under conditions wherein (1) the extender probe is hybridized with and is extended along the target nucleotide sequence to form a duplex, (2) the extended extender probe is dissociated from the duplex, and (3) the primer hybridizes with and is extended along the extended extender probe to form a duplex comprising extended primer, (4) the extended primer is dissociated from the duplex, and (5) the primer hybridizes with and is extended along the extended primer to form a duplex comprising extended primer, and steps (4) and (5) are repeated, wherein steps (a) and (b) are performed concomitantly or wholly or partially sequentially, and (c) examining for the presence of the extended primer.

The invention includes kits comprising in packaged combination (a) a polydeoxynucleotide extender probe having at its 3'-end a sequence hybridizable with a first sequence in a target nucleotide sequence and having a sequence that is homologous to a second sequence of the target nucleotide sequence, wherein in the target nucleotide sequence the second sequence is 5' of, and non-contiguous with, the first sequence and (b) a polydeoxynucleotide primer capable of hybridizing with a sequence that is complementary with the second sequence.

BRIEF DESCRIPTION OF THE FIGURES

FIG. 1 is a schematic representation of a method in accordance with the present invention.

FIG. 2 is a schematic representation of the use of the present method in a single primer amplification.

FIG. 3 is a depiction of M13mp19.

DESCRIPTION OF THE SPECIFIC EMBODIMENTS

The present method allows for the production of a single stranded polynucleotide having an intramolecularly base-paired structure, i.e., two segments that are non-contiguous and complementary with each other. The method has particular application in the area of single primer amplification described above, in which a target sequence in a sample is amplified when such target sequence has an intramolecular base-paired structure or can be converted to such a structure. The present method provides a highly convenient method for converting a polynucleotide sequence of interest to a target sequence having an intramolecularly base-paired structure.

Before proceeding further with a description of the specific embodiments of the present invention, a number of terms will be defined.

Polynucleotide analyte-a compound or composition to be measured which is a polymeric nucleotide which in the intact natural state can have about 20 to 500,000 or more nucleotides and in an isolated state can have about 30 to 50,000 or more nucleotides, usually about 100 to 20,000 nucleotides, more frequently 500 to 10,000 nucleotides. It is thus obvious that isolation of the analyte from the natural state often results in fragmentation. The polynucleotide analytes include nucleic acids from any source in purified or unpurified form including DNA (dsDNA and ssDNA) and RNA, including t-RNA, m-RNA, r-RNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and fragments thereof, and the like. The polynucleotide analyte can be only a minor fraction of a complex mixture such as a biological sample. The analyte can be obtained from various biological material by procedures well known in the art. Some examples of such biological material by way of illustration and not limitation are disclosed in Table I below.

TABLE I

| Microorganisms of interest include: |
|---|
| Corynebacteria |
| *Corynebacterium diphtheria* |
| Pneumococci |
| *Diplococcus pneumoniae* |
| Streptococci |
| *Streptococcus pyrogenes* |
| *Streptococcus salivarus* |

TABLE I-continued

Microorganisms of interest include:

Staphylococci

*Staphylococcus aureus*
*Staphylococcus albus*
Neisseria

*Neisseria meningitidis*
*Neisseria gonorrhea*
Enterobacteriaciae

*Escherichia coli*
*Aerobacter aerogenes*     The colliform
*Klebsiella pneumoniae*     bacteria
*Salmonella typhosa*
*Salmonella choleraesuis*     The Salmonellae
*Salmonella typhimurium*
*Shigella dysenteria*
*Shigella schmitzii*
*Shigella arabinotarda*     The Shigellae
*Shigella flexneri*
*Shigella boydii*
*Shigella sonnei*
Other enteric bacilli

*Proteus vulgaris*
*Proteus mirabilis*     Proteus species
*Proteus morgani*
*Pseudomonas aeruginosa*
*Alcaligenes faecalis*
*Vibrio chloerae*
Hemophilus-Bordetella group     *Rhizopus oryzae*

*Hemophilus influenza, H. ducryi*     *Rhizopus arrhizua* Phycomycetes
*Hemophilus hemophilus*     *Rhizopus nigricans*
*Hemophilus aegypticus*     *Sporotrichum schenkii*
*Hemophilus parainfluenza*     *Flonsecaea pedrosoi*
*Bordetella pertussis*     *Fonsecacea compact*
Pasteurellae     *Fonsecacea dermatidis*

*Pasteurella pestis*     *Cladosporium carrionii*
*Pasteurella tulareusis*     *Phialophora verrucosa*
Brucellae     *Aspergillus nidulans*

*Brucella melitensis*     *Madurella mycetomi*
*Brucella abortus*     *Madurella grisea*
*Brucella suis*     *Allescheria boydii*
Aerobic Spore-forming Bacilli     *Phialophora jeanselmei*

*Bacillus anthracis*     *Microsporum gypseum*
*Bacillus subtilis*     *Trichophyton mentagrophytes*
*Bacillus megaterium*     *Keratinomyces ajelloi*
*Bacillus cereus*     *Microsporum canis*
Anaerobic Spore-forming Bacilli     *Trichophyton rubrum*

*Clostridium botulinum*     *Microsporum adouini*
*Clostridium tetani*     Viruses

*Clostridium perfringens*     Adenoviruses
*Clostridium novyi*     Herpes Viruses

*Clostridium septicum*     Herpes simplex
*Clostridium histolyticum*     Varicella (Chicken pox)
*Clostridium tertium*     Herpes Zoster (Shingles)
*Clostridium bifermentans*     Virus B
*Clostridium sporogenes*     Cytomegalovirus
Mycobacteria     Pox Viruses

*Mycobacterium tuberculosis hominis*     Variola (smallpox)
*Mycobacterium bovis*     Vaccinia
*Mycobacterium avium*     *Poxvirus bovis*
*Mycobacterium leprae*     Paravaccinia
*Mycobacterium paratuberculosis*     *Molluscum contagiosum*
Actinomycetes (fungus-like bacteria)     Picornaviruses

*Actinomyces Isaeli*     Poliovirus
*Actinomyces bovis*     Coxsackievirus
*Actinomyces naeslundii*     Echoviruses TABLE I-continued

| Microorganisms of interest include: | |
|---|---|
| *Nocardia asteroides* | Rhinoviruses |
| *Nocardia brasiliensis* | Myxoviruses |
| The Spirochetes | Influenza (A, B, and C) |
| *Treponema pallidum*  *Spirillum minus* | Parainfluenza (1–4) |
| *Treponema pertenue*  *Streptobacillus monoiliformis* | Mumps Virus |
| | Newcastle Disease Virus |
| *Treponema carateum* | Measles Virus |
| *Borrelia recurrentis* | Rinderpest Virus |
| *Leptospira icterohemorrhagiae* | Canine Distemper Virus |
| *Leptospira canicola* | Respiratory Syncytial Virus |
| Trypanasomes | Rubella Virus |
| Mycoplasmas | Arboviruses |
| *Mycoplasma pneumoniae* | |
| Other pathogens | Eastern Equine Eucephalitis Virus |
| *Listeria monocytogenes* | Western Equine Eucephalitis Virus |
| *Erysipelothrix rhusiopathiae* | Sindbis Virus |
| *Streptobacillus moniliformis* | Chikugunya Virus |
| *Donvania granulomatis* | Semliki Forest Virus |
| *Bartonella bacilliformis* | Mayora Virus |
| Rickettsiae (bacteria-like parasites) | St. Louis Encephalitis Virus |
| *Rickettsia prowazekii* | California Encephalitis Virus |
| *Rickettsia mooseri* | Colorado Tick Fever Virus |
| *Rickettsia rickettsii* | Yellow Fever Virus |
| *Rickettsia conori* | Dengue Virus |
| *Rickettsia australis* | Reoviruses |
| *Rickettsia sibiricus* | Reovirus Types 1–3 |
| | Retroviruses |
| *Rickettsia akari* | Human Immunodeficiency Viruses (HIV) |
| *Rickettsia tsutsugamushi* | Human T-cell Lymphotrophic Virus I & II (HTLV) |
| *Rickettsia burnetti* | Hepatitis |
| *Rickettsia quintana* | Hepatitis A Virus |
| Chlamydia (unclassifiable parasites bacterial/viral) | Hepatitis B Virus |
| | Hepatitis nonA-nonB Virus |
| Chlamydia agents (naming uncertain) | Tumor Viruses |
| Fungi | Rauscher Leukemia Virus |
| *Cryptococcus neoformans* | Gross Virus |
| *Blastomyces dermatidis* | Maloney Leukemia Virus |
| *Hisoplasma capsulatum* | |
| *Coccidioides immitis* | Human Papilloma Virus |
| *Paracoccidioides brasiliensis* | |
| *Candida albicans* | |
| *Aspergillus fumigatus* | |
| *Mucor corymbifer* (*Absidia corymbifera*) | |

The polynucleotide analyte, where appropriate, may be treated to cleave the analyte to obtain a fragment that contains a target polynucleotide sequence, for example, by shearing or by treatment with a restriction endonuclease or other site specific chemical cleavage method. However, it is an advantage of the present invention that the polynucleotide analyte can be used in its isolated state without further cleavage.

For purposes of this invention, the polynucleotide analyte, or a cleaved fragment obtained from the polynucleotide analyte, will usually be at least partially denatured or single stranded or treated to render it denatured or single stranded. Such treatments are well-known in the art and include, for instance, heat or alkali treatment. For example, double stranded DNA can be heated at 90°–100° C. for a period of about 1 to 10 minutes to produce denatured material.

Target polynucleotide sequence—a sequence of nucleotides to be identified, the identity of which is known to an extent sufficient to allow preparation of an extender probe polydeoxynucleotide that will hybridize with at least a portion of such target sequence, usually at least a ten nucleotide segment thereof and preferably at least 15, frequently 20 to 50 nucleotide segment thereof. The target polynucleotide sequence has two non-contiguous, non-complementary nucleotide sequences, S1 and S2, one of which (S1) is the aforesaid portion capable of hybridizing to an extender probe polydeoxynucleotide wherein S2 is 5' of S1. The target polynucleotide sequence usually will contain from about 10 to 5000 or more nucleotides, preferably 20 to 1000 nucleotides. The two non-contiguous, non-complementary nucleotide sequences, S1 and S2, preferably contain from 10 to 100 nucleotides each and are separated by at least ten bases, preferably at least 100, usually 200 to 5000 or more. One target polynucleotide sequence is frequently a part of the polynucleotide analyte. The target polynucleotide sequence will generally be a fraction of a larger molecule or it may be substantially the entire molecule. The minimum number of nucleotides in the target polynucleotide sequence will be selected to assure that the presence of target polynucleotide sequence in a sample will be a specific indicator of the presence of polynucleotide analyte in a sample. Very roughly, the sequence length will usually be greater than about 1.6 log L nucleotides where L is the number of base pairs in the genome of the biologic source of the sample. The maximum number of nucleotides in the target sequence will normally be governed by the length of the polynucleotide analyte and its tendency to be broken by shearing, or other processes during isolation and any procedures required to prepare the sample for assay.

Single stranded polydeoxynucleotide —a sequence of deoxynucleotides that is formed as a result of the present invention. It will normally be comprised at least of two segments or flanking sequences that are non-contiguous and complementary with each other. It may also contain one or more sequences which, when bound to their complementary sequences, are specific binding sites for receptors such as repressors, restriction enzymes, and the like. The first and second segments or flanking sequences are at the 3'-end and 5'-end, respectively, in the single stranded polynucleotide and each comprises at least ten, preferably at least 15, deoxynucleotides, and/or derivatives thereof.

The single stranded polydeoxynucleotide will usually contain from 30 to 50,000 deoxynucleotides, preferably 100 to 2,000 deoxynucleotides, more preferably 500 to 10,000 deoxynucleotides. When the single stranded polydeoxynucleotide is hybridized with a complementary strand, it will frequently form inverted repeats.

Polydeoxynucleotide primer—a polydeoxynucleotide, usually a synthetic deoxynucleotide that is single stranded, containing a sequence at its 3'-end hybridizable with a nucleotide sequence complementary with the sequence S2 of the polynucleotide sequence and having at least 90%, preferably 100%, of the same basic sequence as the second nucleotide sequence of the extender probe. It is also hybridizable, therefore, with a nucleotide sequence complementary with the second segment or flanking sequence of the single stranded polydeoxynucleotide. The number of deoxynucleotides in the hybridizable sequence of polydeoxynucleotide primer should be such that stringency conditions used to hybridize the polydeoxynucleotide primer will prevent excessive random non-specific hybridization. Usually, the number of deoxynucleotides in the polydeoxynucleotide primer will be at least as great as in S2 sequence of the the target polynucleotide sequence, namely, at least ten deoxynucleotides, preferably at least 15 deoxynucleotides and generally from about 10 to 200, preferably 20 to 50, deoxynucleotides.

Member of a specific binding pair ("sbp member")—one of two different molecules, having an area on the surface or in a cavity which specifically binds to and is thereby defined as complementary with a particular spatial and polar organization of the other molecule. The members of the specific binding pair are referred to as ligand and receptor (antiligand). These may be members of an immunological pair such as antigen-antibody, or may be operator-repressor, nuclease-nucleotide biotin-avidin, hormones-hormone receptors, nucleic acid duplexes, IgG-protein A, DNA-DNA, DNA-RNA, and the like.

Ligand—any compound for which a receptor naturally exists or can be prepared.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, repressors, protection enzymes, protein A, complement component Clq, DNA binding proteins or ligands and the like.

Small organic molecule—a compound of molecular weight less than 1500, preferably 100 to 1000, more preferably 300 to 600 such as biotin, fluorescein, rhodamine and other dyes, tetracycline and other protein binding molecules, and haptens, etc. The small organic molecule can provide a means for attachment of a nucleotide sequence to a label or to a support.

Support or surface—a porous or non-porous water insoluble material. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly(ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed.

Binding of sbp members to the support or surface may be accomplished by well-known techniques, commonly available in the literature. See, for example, "Immobilized Enzymes," Ichiro Chibata, Halsted Press, New York (1978) and Cuatrecasas, *J. Biol. Chem.*, 245:3059 (1970). The surface can have any one of a number of shapes, such as strip, rod, particle, including bead, and the like.

The surface will usually be polyfunctional or be capable of being polyfunctionalized or be capable of binding an oligonucleotide or an sbp member through specific or non-specific covalent or non-covalent interactions. A wide variety of functional groups are available or can be incorporated. Functional groups include carboxylic acids, aldehydes, amino groups, cyano groups, ethylene groups, hydroxyl groups, mercapto groups and the like. The manner of linking a wide variety of compounds to particles is well known and is amply illustrated in the literature. See for example Cautrecasas, *J. Biol. Chem* 245,3059 (1970). The length of a linking group to the oligonucleotide or sbp member may vary widely, depending upon the nature of the compound being linked, the effect of the distance between the compound being linked and the particle on the hybridization of the sequences and the like. The oligonucleotide or sbp member will be substantially bound to the outer surface of the particle.

Particles employed as the surface can be fluorescent either directly or by virtue of fluorescent compounds or fluorescers bound to the particle in conventional ways. The fluorescers will usually be dissolved in or bound covalently or non-covalently to the particle and will frequently be substantially uniformly bound through the particle. Fluoresceinated latex particles are taught in U.S. Pat. No. 3,853,987.

Label or reporter group or reporter molecule—a member of the signal producing system. Usually the label or reporter group or molecule is conjugated to or becomes bound to a probe or a polydeoxynucleotide primer and is capable of being detected directly or, through a specific binding reaction, and can produce a detectible signal. Labels include a polynucleotide primer or specific polynucleotide sequence that can provide a template for amplification or ligation or act as a ligand such as for a repressor protein. Preferably, the polydeoxynucleotide primer will have, or be capable of having, a label. In general, any label that is detectable can be used. The label can be isotopic or nonisotopic, usually non-isotopic, and can be a catalyst, such as an enzyme, a polynucleotide coding for a catalyst, promoter, dye, fluorescent molecule, chemiluminescer, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectible group, and the like. The label is a member of a signal producing system and can generate a detectable signal either alone or together with other members of the signal producing system. The label can be bound directly to a nucleotide sequence or can become bound thereto by being bound to an sbp member complementary to an sbp member that is bound to a nucleotide sequence.

Signal Producing System—The signal producing system may have one or more components, at least one component being the label or reporter group. The signal producing system generates a signal that relates to the presence or amount of target polynucleotide sequence or a polynucleotide analyte in a sample. The signal producing system includes all of the reagents required to produce a measurable signal. When the label is not conjugated to a nucleotide sequence, the label is normally bound to an sbp member complementary to an sbp member that is bound to or part of a nucleotide sequence. Other components of the signal producing system may be included in a developer solution and can include substrates, enhancers, activators, chemiluminiscent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like. The signal producing system provides a signal detectable by external means, by use of electromagnetic radiation, desirably by visual examination.

The signal-producing system can include at least one catalyst, usually an enzyme, and at least one substrate and may include two or more catalysts and a plurality of substrates, and may include a combination of enzymes, where the substrate of one enzyme is the product of the other enzyme. The operation of the signal producing system is to produce a product which provides a detectable signal related to the amount of polynucleotide analyte in the sample.

A large number of enzymes and coenzymes useful in a signal producing system are indicated in U.S. Pat. No. 4,275,149, columns 19 to 23, and U.S. Pat. No. 4,318,980, columns 10 to 14, which disclosures are incorporated herein by reference. A number of enzyme combinations are set forth in U.S. Pat. No. 4,275,149, columns 23 to 28, which combinations can find use in the subject invention. This disclosure is incorporated herein by reference.

Of particular interest are enzymes which involve the production of hydrogen peroxide and the use of the hydrogen peroxide to oxidize a dye precursor to a dye. Particular combinations include saccharide oxidases, e.g., glucose and galactose oxidase, or heterocyclic oxidases, such as uricase and xanthine oxidase, coupled with an enzyme which employs the hydrogen peroxide to oxidize a dye precursor, that is, a peroxidase such as horse radish peroxidase, lactoperoxidase, or microperoxidase. Additional enzyme combinations may be found in the subject matter incorporated by reference. When a single enzyme is used as a label, other enzymes may find use such as hydrolases, transferases, and oxidoreductases, preferably hydrolases such as alkaline phosphatase and β-galactosidase. Alternatively, luciferases may be used such as firefly luciferase and bacterial luciferase.

Illustrative coenzymes which find use include NAD[H]; NADP[H], pyridoxal phosphate; FAD[H]; FMN[H], etc., usually coenzymes involving cycling reactions, see particularly U.S. Pat. No. 4,318,980.

The product of the enzyme reaction will usually be a dye or fluorescer. A large number of illustrative fluorescers are indicated in U.S. Pat. No. 4,275,149, columns 30 and 31, which disclosure is incorporated herein by reference.

The signal producing system can include one or more particles, which are insoluble particles of at least about 50 nm and not more than about 50 microns, usually at least about 100 nm and less than about 25 microns, preferably from about 0.2 to 5 microns, diameter. The particle may be organic or inorganic, porous or non-porous, preferably of a density approximating water, generally from about 0.7 to about 1.5 g/ml, and composed of material that can be transparent, partially transparent, or opaque.

The organic particles will normally be comprised of polymers, either addition or condensation polymers, which are readily dispersible in the assay medium. The surface of particles will be adsorptive or functionalizable so as to bind, either directly or indirectly, an oligonucleotide or an sbp member. The nature of particles is described above.

Fluorescers of interest will generally emit light at a wavelength above 350 nm, usually above 400 nm and preferably above 450 nm. Desirably, the fluorescers have a high quantum efficiency, a large Stokes shift and are chemically stable under the conditions of their conjugation and use. The term fluorescer is intended to include substances that emit light upon activation by electromagnetic radiation or chemical activation and includes fluorescent and phosphorescent substances, scintillators, and chemiluminescent substances.

Fluorescers of interest fall into a variety of categories having certain primary functionalities. These primary functionalities include 1- and 2-aminonaphthalene, p,p-diaminostilbenes, pyrenes, quaternary phenanthridine salts, 9-aminoacridines, p, p'-diaminostilbenes immines, anthracenes, oxacarboxyanine, merocyanine, 3-aminoequilenin, perylene, bis-benzoxazole, bis-p-oxazolyl benzene, 1,2-benzophenazine, retinal, bis-3-aminopyridinium salts, hellebrigenin, tetracycline, sterophenol, benzimidazolylphenylamine, 2-oxo-3-chromen, indole, xanthene, 7-hydroxycoumarin, 4,5-benzimidazoles, phenoxazine, salicylate, strophanthidin, porphyrins, triarylmethanes, flavin and rare earth chelates oxides and salts. Exemplary fluorescers are enumerated in U.S. Pat. No. 4,318,707, columns 7 and 8, the disclosure of which is incorporated herein by reference.

Additionally, energy absorbent or quenching particles can be employed which are solid insoluble particles of at least about 50 nm in diameter capable of quenching the fluorescence of the fluorescent particle when within the distance resulting from hybridization of a probe with the polynucleotide analyte or from specific binding between members of specific binding pairs. The quenching particle may be the same or different, usually different, from the fluorescent particle. Normally, the quenching particle will provide a substantial quenching at a distance of more than about 50 Å, preferably more than about 500 Å, more preferably more than about 2000 Å, where the distance is measured from the surfaces of the particles.

Many different types of particles may be employed for modulating light emission. Of particular interest are carbon particles, such as charcoal, lamp black, graphite, colloidal carbon and the like. Besides carbon particles metal sols may also find use, particularly of the noble metals, gold, silver, and platinum. Other metal-derived particles may include metal sulfides, such as lead, silver or copper sulfides or metal oxides, such as iron or copper oxide.

An alternative source of light as a detectible signal is a chemiluminescent source. The chemiluminescent source involves a compound which becomes electronically excited by a chemical reaction and may then emit light which serves as the detectible signal or donates energy to a fluorescent acceptor.

A diverse number of families of compounds have been found to provide chemiluminescence under a variety of conditions. One family of compounds is 2,3-dihydro-1,4-phthalazinedione. The most popular compound is luminol, which is the 5-amino analog of the above compound. Other members of the family include the 5-amino-6,7,8-trimethoxy- and the dimethylamine-[ca]benz analog. These compounds can be made to luminesce with alkaline hydrogen peroxide or calcium hypochlorite and base. Another family of compounds is the 2,4,5-triphenylimidazoles, with lophine as the common name for the parent product. Chemiluminescent analogs include para-dimethylamino- and para-methoxy-substituents. Chemiluminescence may also be obtained with oxilates, usually oxalyl, active esters, e.g., p-nitrophenyl and a peroxide, e.g., hydrogen peroxide, under basic conditions. Alternatively, luciferine may be used in conjunction with luciferase or lucigenins.

Ancillary Materials—Various ancillary materials will frequently be employed in the assay in accordance with the present invention. For example, buffers will normally be present in the assay medium, as well as stabilizers for the assay medium and the assay components. Frequently, in addition to these additives, proteins may be included, such as albumins, organic solvents such as formamide, quaternary ammonium salts, polycations such as dextran sulfate, surfactants, particularly non-ionic surfactants, binding enhancers, e.g., polyalkylene glycols, or the like.

Deoxynucleoside triphosphates—a deoxynucleoside having a 5'-triphosphate substituent. The deoxynucleosides are pentose sugar derivatives of nitrogenous bases of either purine or pyrimidine derivation, covalently bonded to the 1'-carbon of the pentose sugar. The purine bases include adenine(A), guanine(G), inosine, and derivatives and analogs thereof. The pyrimidine bases include cytosine (C), thymine (T), uracil (U), and derivatives and analogs thereof.

The derivatives and analogs are exemplified by those that are recognized and polymerized in a similar manner to the underivitized nucleoside triphosphates. Examples of such derivatives or analogs by way of illustration and not limitation are those which are modified with a reporter group, biotinylated, amine modified, radiolabeled, alkylated, and the like and also include thiophosphate, phosphite, ring atom modified derivatives, and the like. The reporter group can be a fluorescent group such as fluoroscein, a chemiluminescent group such as luminol, a terbium chelator such as N-(hydroxyethyl) ethylenediaminetriacetic acid that is capable of detection by delayed fluorescence, and the like.

Polydeoxynucleotide polymerase—a catalyst, usually an enzyme, for forming an extension of the polydeoxynucleotide primer along a DNA template including the single stranded polydeoxynucleotide where the extension is complementary thereto. The polydeoxynucleotide polymerase is a template dependent polydeoxynucleotide polymerase and utilizes the deoxynucleoside triphosphates as building blocks for extending the 3'-end of the polydeoxynucleotide primer to provide a sequence complementary with the single stranded polydeoxynucleotide. Usually, the catalysts are enzymes, such DNA polymerases such as, for example, prokaryotic DNA polymerase (I, II, or III), T4 DNA polymerase, T7 DNA polymerase, Klenow fragment, and the like derived from any source such as cells, bacteria, such as $E.\ coli$, plants, animals, virus, thermophilic bacteria, and so forth. Where the polynucleotide or target polynucleotide sequence is RNA, reverse transcriptase would be included to facilitate extension of the extender probe along the polynucleotide or target nucleotide sequence.

Wholly or partially sequentially—when the sample and various agents utilized in the present invention are combined other than concomitantly (simultaneously), one or more may be combined with one or more of the remaining agents to form a subcombination. Each subcombination can then be subjected to one or more steps of the present method. Thus, each of the subcombinations can be incubated under conditions to achieve one or more of the desired results.

Hybridization (hybridizing) and binding—in the context of nucleotide sequences these terms are used interchangeably herein. The ability of two nucleotide sequences to hybridize with each other is based on the degree of complementarity of the two nucleotide sequences, which in turn is based on the fraction of matched complementary nucleotide pairs. The more nucleotides in a given sequence that are complementary to another sequence, the greater the degree of hybridization of one to the other. The degree of hybridization also depends on the viscosity conditions or stringency which include temperature, solvent ratios, salt concentrations, and the like.

Homologous—two sequences are homologous where the sequences each have at least 90%, preferably 100%, of the same or analogous base sequence where thymine (T) and uracil (U) are considered the same. Thus, the ribonucleotides A, U, C and G are taken as analogous to the deoxynucleotides dA, dT, dC, and dG. Homologous sequences can both be DNA or one can be DNA and the other RNA.

Extender probe—is comprised of a single strand of two sequences of deoxynucleotides having at its 3'-end one of such sequences (EP1) preferably at least ten consecutive deoxynucleotides thereof and capable of hybridizing with a first polynucleotide sequence (S1) of a polynucleotide including a target polynucleotide sequence, having two non-contiguous, non-complimentary nucleotide sequences wherein S1 is 3' of the second of such sequences. Capability of hybridizing occurs by virtue of being partially or completely, usually completely, complementary to the first polynucleotide sequence such that the first polynucleotide sequence will become bound to EP1. Usually, the extender probe is a synthetic oligonucleotide.

The major criteria for choosing EP1 are: (1) The sequence should be reliable, that is, it should be closely or exactly complementary S1 and should be of sufficient length to provide stable and specific binding. (2) The 3'-end must form, or be capable of forming, a free 3'-hydroxyl group. The minimum binding sequence will usually be at least 10, normally at least 15, preferably 20–50, deoxynucleotides in length. In general, EP1 will be about 30 to 100 deoxynucleotides. The combined length of the first and second polydeoxynucleotide sequences of the extender probe is at least about 20 nucleotides, preferably about 40 to 200 nucleotides, in length.

The second polydeoxynucleotide sequence of the extender probe (EP2) is a sequence of deoxynucleotides homologous to a second polynucleotide sequence (S2) of a target polynucleotide having two non-contiguous, non-complementary nucleotide sequences where S2 is 5' of S1. EP2 is at least 10 nucleotides, usually at least 15, preferably 20–50 deoxynucleotides, in length. In general EP2 will be about 30 to 100 deoxynucleotides.

The extender probe may contain additional receptor binding or spacer sequences or other sequences located between EP1 and EP2 or at the end of EP2.

Non-contiguous-sequences are non-contiguous, there being at least one usually at least 10 deoxynucleotides present in the target polydeoxynucleotide sequence between the two segments or between two sequences, S1 and S2, of a polynucleotide.

Contiguous—sequences are considered to be contiguous when there are no deoxynucleotides between two segments or between two sequences of a polynucleotide.

Copy—means a sequence that is a direct copy of a single stranded polydeoxynucleotide sequence as differentiated from a sequence that is complementary to the sequence of such single stranded polynucleotide. In single primer amplification conducted in conjunction with the present invention, a complementary sequence of a single stranded polydeoxynucleotide is produced initially as the result of the extension of the polydeoxynucleotide primer and a sequence that is a direct copy of the single stranded polydeoxynucleotide is subsequently obtained from the aforementioned complementary sequence.

Means for extending an extender probe—an extender probe having an extendable 3'-terminus can be extended by combining the extender probe hybridized to a polynucleotide, such as a target polynucleotide sequence, having two segments as described above with a polydeoxynucleotide polymerase and deoxynucleoside triphosphates under conditions for extending the extender probe. In this way the extender probe is extended along the single stranded polynucleotide to form a duplex comprising the extended extender probe. Extension in this fashion provides the requisite fidelity between the two strands so that subsequent amplification of the extended extender probe or extended polydeoxynucleotide primer provides accurate detection of the target of interest.

Means for extending a primer—a polydeoxynucleotide primer having an extendable 3'-terminus can be extended by combining the primer hybridized to extended extender probe or extended primer with a polydeoxynucleotide polymerase and deoxynucleoside triphosphates under conditions for extending the primer. In this way the primer is extended along the extended extender probe or extended primer to form a duplex comprising the extended primer. Extension in this fashion provides the requisite fidelity between the extended primer and the polynucleotide so that accurate detection of target analytes can be achieved.

The method is depicted schematically in Scheme in FIG. 1.

EP1 of the extender probe hybridizes with S1 of the polynucleotide. EP2 is homologous with S2. The extender probe is extended along A to produce an extended extender probe B containing sequence S'2 which is complementary to S2. B now contains EP2 and S'2, which are hybridizable with each other.

The method find use in single primer amplification. In this regard a combination is provided comprising a polydeoxynucleotide primer capable of hybridizing at least at its 3'-end with a nucleotide sequence complementary to S2 under conditions where (1) the extended extender probe is rendered single stranded, (2) the polydeoxynucleotide primer hybridizes with and is extended along the extended extender probe to form a duplex comprising extended primer, (3) the extended primer is dissociated from the duplex, and (4) the primer hybridizes with and is extended along the extended primer to form a duplex comprising extended primer. Steps (3) and (4) are repeated. Preferably, the concentration of the extender probe is substantially lower than that of the polydeoxynucleotide primer. By "substantially lower" is meant that the concentration of extender probe relative to primer is such that single primer amplification, as described herein, occurs rather than a PCR amplification. Preferably, the concentration of the extender probe is less than one percent that of the polydeoxynucleotide primer.

The use of the present method in single primer amplification is depicted in FIG 2.

Polydeoxynucleotide primer P has a sequence at its 3'-end (PS) that hybridizes with S'2, which is complementary to S2. P can also comprise a label W. P is hybridized with and extended along extended extender probe B (which has been dissociated from its duplex) to form extended primer C comprising sequences S"2 and S'2. B and C are dissociated and P hybridizes with S'2 of C and S'2 of B and P is extended along B and C to yield C and C', respectively. C' has sequences S'2 and S"2. The duplexes are dissociated and P is hybridized with and extended along C' and C to yield C' and C'. Further, repetition results in multiple copies of C', which can be detected because of the presence of label W. Copies of B and C are minimized because of the substantially lower concentration of the extender probe to that of the polydeoxynucleotide primer. As a result single primer amplification occurs, rather than a PCR amplification. The product of single primer amplification is detected, not the product of PCR amplification.

When the extender probe and the primer are both used at high concentrations, there is the capability to produce a PCR amplification of the target, but the PCR product will usually differ from the single primer amplification product, and its formation will reduce the amount of the single primer amplification product. Further, by reducing the number of primers that can randomly prime contaminating DNA, single primer amplification gives more selective amplification of the target than PCR. This was shown by directly comparing amplified DNA products between single primer amplification in accordance with the present invention and PCR over the same region of target DNA. Under identical reaction conditions, PCR resulted in a higher ratio of irrelevant amplification products to amplified target DNA than that obtained with single primer amplification in the present invention. Utilizing a substantially lower concentration of extender probe also provides for conservation of materials and reduced costs.

Another embodiment of the present invention is a method for producing multiple copies of a single stranded polydeoxynucleotide having two segments that are non-contiguous and complementary with each other. A combination is provided, either concomitantly or wholly or partially sequentially, comprising a polynucleotide having two non-contiguous, non-complementary nucleotide sequences, S1 and S2, wherein S2 is 5' of S1 and is at least ten nucleotides long, an extender probe comprised of two deoxynucleotide sequences, wherein the sequence at the 3'-end of the extender probe is hybridizable with S1 and the other of the nucleotide sequences is homologous to S2 and not complementary to the polynucleotide, a polydeoxynucleotide primer capable of hybridizing at least at its 3'-end with a nucleotide sequence complementary to S2, DNA polymerase, and deoxynucleoside triphosphates. The combination is provided under conditions where (a) the extender probe is extended along the polynucleotide to form a duplex, (b) the extended extender probe is dissociated from the duplex, (c) the polydeoxynucleotide primer hybridizes with and is extended along the extended extender probe to form a second duplex comprising extended primer (d) the extended primer is dissociated from the second duplex, and (e) the primer hybridizes with and is extended along the extended primer to form a duplex comprising extended primer, and steps (d) and (e) are repeated at least three times The concentration of the extender probe is less than one percent that of the polynucleotide primer. Preferably at least a fifteen nucleotide sequence of the extender probe hybridizes with S1. Preferably, also, the polydeoxynucleotide primer contains at least a fifteen deoxynucleotide sequence capable of hybridizing with a sequence complementary to S2.

Another embodiment of the invention concerns a method for detecting the presence of a target nucleotide sequence in a medium suspected of containing the target nucleotide sequence. The target nucleotide sequence has two non-contiguous, non-complementary nucleotide sequences S1 and S2. S2 is 5' of S1 and at least 10 nucleotides long. A combination is provided, either concomitantly or wholly or partially sequentially, comprising the medium, an extender probe having two deoxynucleotide sequences wherein the sequence at the 3'-end of the extender probe is hybridizable with S1 and the other of the deoxynucleotide sequences is homologous to S2 and not complementary to the target nucleotide sequence, a Polydeoxynucleotide primer capable of hybridizing with a nucleotide sequence complementary to S2, DNA polymerase and deoxynucleoside triphosphates. Conditions are selected wherein (1) the extender probe is extended along the polynucleotide to form a duplex, (2) the extended extender probe is dissociated from the duplex, (3) the primer hybridizes with and is extended along the extended extender probe to form a duplex comprising extended primer, (4) the extended primer is dissociated from the duplex, and (5) the primer hybridizes with and is extended along the extended primer to form a duplex comprising extended primer. Steps (4) and (5) are repeated and an examination for the presence of the extender primer is carried out. The presence of the extended primer indicates the presence of the target nucleotide sequence.

Preferably, S1 and S2 each respectively contain from 10 to 100 nucleotides. The method has application where the target nucleotide sequence is DNA or RNA. In one aspect the polydeoxynucleotide primer is labeled with a reporter molecule. The polydeoxynucleotide primer can contain a nucleotide sequence other than the sequence that hybridizes with the sequence complementary to S2. The extended primer can be detected by examining for a reporter molecule covalenty bonded to a nucleotide sequence that is complementary to a portion of the target nucleotide sequence other than S1 or S2.

Another embodiment of the invention concerns a method for detecting the presence of a polynucleotide analyte in a sample suspected of containing the polynucleotide analyte. A medium containing the sample is treated as described above to form a single stranded target nucleotide sequence from the polynucleotide analyte, if present. The target nucleotide sequence has two non-contiguous, non-complementary nucleotide sequences S1 and S2 wherein S2 is 5' of S1, and is at least ten nucleotides long. The medium is combined with an extender probe having two deoxynucleotide sequences. The sequence at the 3' end of the extender probe is hybridizable with S1. The other of the deoxynucleotide sequences is homologous to S2 and not complementary to the target sequence. A polydeoxynucleotide primer capable of hybridizing with a nucleotide sequence complementary to S2, as well as deoxynucleoside triphosphates, and DNA template dependent polydeoxynucleotide polymerase are also combined. Conditions are chosen such that (1) the extender probe is hybridized with and is extended along the target nucleotide sequence to form a duplex, (2) the extended extender probe is dissociated from the duplex, (3) the primer hybridizes with and is extended along the extended sequence to form a second duplex comprising extended primer, (4) the extended primer is dissociated from the duplex, and (5) the primer hybridizes with and is extended along said extended primer to form a duplex comprising extended primer. Steps (4) and (5) are repeated and steps (a) and (b) are performed concomitantly or wholly or partially sequentially. Then, an examination is conducted for the presence of the extended primer, the presence thereof indicating the presence of the polynucleotide analyte. Steps (4) and (5) are repeated a least three times, preferably, at least 10 times; usually it is preferable that the number of repetitions be less than 30. Generally, steps (4) and (5) are repeated a number of times sufficient to provide an accurate detection of the polynucleotide analyte. Where the polynucleotide analyte is RNA the medium also includes reverse transcriptase.

In carrying out the method of forming the single stranded polydeoxynucleotide and the amplification an aqueous medium will be employed. Other polar cosolvents may also be employed, usually oxygenated organic solvents of from 1–6, more usually from 1–4, carbon atoms, including alcohols, ethers and the like. Usually these cosolvents will be present in less than about 70 weight percent, more usually in less than about 30 weight percent.

The pH for the medium will usually be in the range of about 4.5 to 9.5, more usually in the range of about 5.5–8.5, and preferably in the range of about 6–8. The pH and temperature are chosen and varied, as the case may be, so as to provide for either simultaneous or sequential dissociation of any internally hybridized sequences, hybridization of the extender probe and the polynucleotide and the polydeoxynucleotide primer with extended extender probe or extended primer, extension of the extender probe and primer, dissociation of the extended probe and primer, hybridization of extended primer with primer, extension of the so-hybridized primer, and dissociation of extended primer and repetition of the latter steps. In some instances, a compromise will be made between these considerations depending on whether the above steps are performed sequentially or simultaneously. Various buffers may be used to achieve the desired pH and maintain the pH during the determination. Illustrative buffers include borate, phosphate, carbonate, Tris, barbital and the like. The particular buffer employed is not critical to this invention but in individual methods one buffer may be preferred over another.

Moderate temperatures are normally employed for carrying out the method. Normally, in conducting the method the medium will be cycled between two or three temperatures.

The temperatures for the method will generally range from about 10° to 100° C., more usually from about 40° to 98° C., preferably 50° to 97° C. The exact temperatures can be varied depending on the salt concentration, pH, solvents used, chain length and composition of the target polynucleotide sequence and the primer. Relatively low temperatures of from about 30° to 65° C. can be employed for the extension steps, while denaturation and hybridization can be carried out at a temperature of from about 50° to 100° C.

The time period for carrying out the method of the invention will generally be long enough to achieve a desired number of copies of the extended primer or a sequence complementary thereto. This, in turn, depends on the purpose for which the amplification is conducted, such as, for example, an assay for a polynucleotide analyte. Generally, the time period for conducting the method will be from about 1 to 10 minutes per cycle and any number of cycles can be used from 1 to as high as 200 or more, usually 1 to 80, frequently 20–80. As a matter of convenience it will usually be desirable to minimize the time period and the number of cycles. In general, the time period for a given degree of amplification can be shortened, for example, by selecting concentrations of nucleoside triphosphates sufficient to saturate the polynucleotide polymerase and by increasing the concentrations of polynucleotide polymerase and polynucleotide primer. Generally, the time period for conducting the method will be from about 5 to 200 min. As a matter of convenience, it will usually be desirable to minimize the time period.

The above conditions may also be chosen for forming a target polynucleotide sequence from a polynucleotide analyte.

The amount of the single stranded polydeoxynucleotide or target polynucleotide sequence which is to be copied can be as low as one or two molecules in a sample but will generally vary from about $10^2$ to $10^{10}$, more usually from about $10^3$ to $10^8$ molecules in a sample. The amount of the polydeoxynucleotide primer will be at least as great as the number of copies desired and will usually be $10^{-13}$ to $10^{-8}$ moles per sample, where the sample is 10–1,000 µL. Usually, the primer will be present in at least $10^{-9}$M, preferably $10^{-7}$M, and more preferably at least about $10^{-6}$M. Preferably, the concentration of the polynucleotide primer is substantially in excess over, preferably at least 100 times greater than, the concentration of the single stranded polynucleotide.

The concentration of the extender probe, as mentioned above, should be substantially less than that of the primer. Preferably, the extender probe concentration is less than one percent of that of the primer, more preferably less than 0.1% that of the primer usually the extender probe concentration will be less than 1 nmolar, frequently less than 0.1 nmolar (nM) whereas the primer concentration will usually be greater than 10 nmolar, usually at least 100 nmolar. Preferably, the concentration of primer is greater than 100 nM while that of the extender probe is less than 1 nM.

The final concentration of each of the reagents will normally be determined empirically to optimize the number of the copies of the extended primer.

The concentration of the deoxynucleoside triphosphates in the medium can vary widely; preferably, these reagents are present in an excess amount. The deoxynucleoside triphosphates will usually be present in $10^{-6}$ to $10^{-2}$M, preferably $10^{-5}$ to $10 -3$M.

The concentration of the template-dependent polynucleotide polymerase will usually be determined empirically. Preferably, a concentration will be used that is sufficient such that further increase in the concentration will not decrease the time for the amplification by over 5-fold, preferably 2-fold. The primary limiting factor generally is the cost of the reagent.

The order of combining of the various reagents to form the combination may vary. Generally, the target nucleotide sequence is obtained from a sample containing such sequence or a polynucleotide analyte that has been treated to obtain such sequence. Generally, the target polynucleotide sequence and the extender probe are combined with a pre-prepared combination of polynucleotide primer, deoxynucleoside triphosphates, and template-dependent polydeoxynucleotide polymerase. However, simultaneous addition of all of the above, as well as step-wise or sequential orders of addition, may be employed.

The concentration and order of addition of reagents and conditions for the method are governed generally by the desire to maximize the number of copies of the extended primer and the rate at which such copies are formed. Generally, it is desirable to increase the number of copies of the extended primer by at least a factor of $10^2$, preferably a factor of $10^4$, more preferably $10^6$ or more.

The order of combining of the various reagents to form the combinations referred to above for determination of a polynucleotide analyte may vary and can be concomitant or simultaneous or wholly or partially sequential. Generally, a sample containing a polynucleotide analyte is obtained and treated to yield a target nucleotide sequence. The target polydeoxynucleotide sequence can be combined with the extender probe and the two hybridized. Next, the extender probe is extended along the target nucleotide sequence in the presence of deoxynucleotide triphosphates and DNA polymerase. A pre-prepared combination of deoxynucleoside triphosphates, and DNA polymerase can be utilized. The combination can also include a polydeoxynucleotide primer. Simultaneous addition of the above, as well as step-wise or sequential orders of addition, may be employed. The concentration and order of addition of reagents and conditions for the method are governed generally by the considerations mentioned above. In carrying out the method of the invention as applied to the detection of a polynucleotide analyte, the considerations as to media, pH, temperature, and times can be as described above.

The concentration of the target polynucleotide analyte can be as low as possibly one molecule, preferably at least $10^{-21}$M in a sample but will generally vary from about $10^{10}$M to $10^{-19}$M, more usually from about $10^{-14}$ to $10 -19$M.

While the concentrations of the various reagents will generally be determined by the concentration range of interest of the polynucleotide analyte, the final concentration of each of the reagents will normally be determined empirically to optimize the sensitivity of the assay over the range of interest. The concentration of the other reagents in an assay generally will be determined following the same principles as set forth above for the amplification method. The primary consideration is that a sufficient number of copies of extended primer be produced in relation to the polynucleotide analyte sequence so that such copies can be readily detected and provide an accurate determination of the polynucleotide analyte.

The copies of extended primer can be detected in numerous ways. For example, in the present method, the molecules of the Polydeoxynucleotide primer can be labeled with a ligand W' and W' can then be detected.

In another example the label can be a small organic molecule, a polynucleotide sequence, a protein, or the like.

Upon amplification, a mixture of duplexes is obtained having label at an end. Duplexes can be detected by causing the molecule to bind to a surface to which is bound a receptor for the ligand. After removal of unbound material, the support is examined for the presence of a detectable label. The presence thereof indicating the presence of polynucleotide analyte in the sample.

In another approach, sequences can be selected because a synthetic or natural receptor exists that can bind to the hybridized sequences. The sequences may be introduced by including them between EP1 and EP2 of the extender probe described above. Alternatively, they can be introduced as labels at the 5'-end of a portion of the polydeoxynucleotide primer molecules. The tetracycline repressor is such a receptor. This protein binds to the tetracycline operator and the hybridized sequences can be selected to comprise some or all of this operator. The repressor is bound to a solid support and used to absorb and concentrate the amplification product from the amplification reaction solution. The bound product can then be detected by hybridizing a nucleic acid probe to the amplified target sequence when the probe is bound to a detecable label. When the label can be detected by changes in the physical property of the adsorbent such as electrical properties, optical properties, acoustic wave modulation, and the like.

Other operator-repressor pairs can be used including, for example, the lac repressor and operator which have been used as a ligand and receptor for capture of DNA duplexes and the tryptophane repressor and operator.

In another approach bromodeoxyuridine can be incorporated into a portion of the polydeoxynucleotide primer molecules and antibodies to bromodeoxyuridine can be employed. Detection of the bound sequence can be accomplished by any of the above methods.

In a preferable approach for detection of the extended primer copies, the copies are simultaneously or sequentially denatured by heating or use of denaturing solvents and solutes and caused to bind to a support by, for example, one of the above methods. The support is then contacted with a probe comprised of a nucleic acid sequence and a label or receptor binding site. The nucleic acid sequence is complementary to at least the portion of the extended primer copies. The presence of the extended primer copy is then indicated by the presence of the label or receptor binding site on the support.

Other assay formats and detection formats are disclosed in U.S. patent applications Ser. Nos. 07/229,282 and 07/399,795 filed Jan. 19, 1989, and Aug. 29, 1989, respectively, which have been incorporated herein by reference.

Any standard method for specifically detecting double strand nucleic acid sequences can be used.

One method for detecting nucleic acids is to employ nucleic acid probes. This method generally involves immobilization of the target nucleic acid on a solid support such as nitrocellulose paper, cellulose paper, diazotized paper, or a nylon membrane. After the target nucleic acid is fixed on the support, the support is contacted with a suitably labelled probe nucleic acid for about ten minutes to forty-eight hours. After the above time period, the solid support is washed several times to remove unbound probe and the hybridized material is detected by autoradiography or spectroscopic methods.

One method utilizing probes is described in U.S. patent application Ser. No. 773,386, filed Sep. 6, 1985, now U.S. Pat. No. 4,868,104, the disclosure of which is incorporated herein by reference. The method comprises combining in an assay medium the sample and first and second polynucleotide reagents complementary to the nucleic acid fragment. Each of the first and second reagents hybridize with a different region of nucleic acid fragment. The first reagent contains means for rendering the first reagent non-covalently polymerizable. The second reagent contains means for rendering the second reagent detectable. The sample and the first and second reagents are combined in the assay medium under conditions for polymerizing the first reagent wherein the second reagent becomes bound to the polymerized first reagent only when the DNA fragment is present in the sample. A determination is then made as to whether the second reagent has become bound to the polymerized first reagent.

In order to separate the copies of extended primer from other components in an assay mixture containing a sample it can be desirable, and indeed preferable in some circumstances, that the polynucleotide or polydeoxynucleotide primer has, or is capable of having, means for immobilizing the sequence. Generally, this means for immobilizing involves a support. The sequence in question can be treated to bind the sequence to a support prior to the use of this sequence in the method of the present invention. Numerous methods are known for binding nucleotide sequences to solid supports. For example see T. Goldkorn et al., *Nucleic Acids Research* (1986) 14:9171–9191 and the references contained therein. Generally, the procedures for attaching the nucleotide sequence to supports involve chemical modifications of some of the nucleotides in the sequence whereby the sequence can then be attached to the support. Preferably, the bond between the support and the nucleotide sequence will be covalent, more preferably involving a linking group between the nucleotide sequence the support. For example, the support can be treated to introduce maleimide groups and the nucleotide sequence can be treated to introduce a thiol group. The thiol group is reactive with the activated olefin of the maleimide group and in such a fashion the nucleotide sequence can be covalently bound to the support. Examples of other such linking groups are cellulose derivatized with diazobenzyloxymethyl groups as described by Noyes, B. E. and Stark, G. R., *Cell* 5, 301 (1975) and Alwine, J. C., et al., *Proc. Natl. Acad. Sci., U.S.A.* 74, 5350 (1977), and cellulose derivatized with o-aminophenylthioether, such as described by Seed, B., *Nucleic Acids Res.*, 10, 1799 (1982).

If the nucleotide sequence is not initially bound to a support, it may be desirable that one of the two sequences become bound to a support at some time during the method of the invention, preferably, prior to the detection of the extended primer copies. Accordingly, the support and one of the nucleotide sequences must contain reactive groups which can provide a linkage between the support and the nucleotide sequence. The nature of the reactive groups will be such as to be compatible with the method of the present invention.

One such system is that described above where the support would contain maleimide groups and the nucleotide sequence would contain a thiol group. In another embodiment the nucleotide sequence and the support can contain complementary specific binding pair members such as biotin-avidin and the like. Thus, the method of the present invention can be run in solution and at the appropriate time the support can be introduced whereupon the complementary sbp members will bind. After the support is washed, to remove unbound material, further reactions or determinations can be carried out.

Other examples of such systems are repressor-operator interactions where one of the nucleotide sequences is captured at the solid surface by its sequence specific interaction with a specific repressor or modulator protein immobilized on the solid surface. An advantage of this embodiment of the capture phase is that in some cases release of the operator DNA from the repressor can be accomplished by treating the complex with an inducer molecule. For example, the tetracycline repressor may be immobilized on a solid surface so that an operator sequence present on one or the other of the nucleotide sequences is specifically captured and retained when the solution is contacted to the surface. The surface may then be washed to eliminate any non-specific binding and finally the operator containing nucleotide may be released from the surface by contacting the repressor-operator complex bound at the surface with an inducer molecule (tetracycline or one of its active analogs in this case).

The inducer molecule may be the "natural inducer" in the sense that it is structurally identical with the molecule in nature that causes dissociation of the biological/regulatory repressor-operator complex or it may be a synthetic analog of the natural inducer with similar or enhanced binding and complex dissociation activity. Examples of the above include the tetracycline repressor-operator interaction and its dissociation by tetracycline such as described by Hillen, W., et al *J. Mol. Biol.,* 169,707–721 (1983) and Klock, G., et al., *J. Bact.,* 161, 326–332 (1985).

In the situation where the nucleotide sequence is covalently attached to the support, it may be desirable to remove the attached sequence from the support, such as, for example, in order to amplify or clone the sequence. In this situation it is desirable to introduce a cleavable group between the nucleotide sequence and the support. Exemplary of such cleavable groups are pyrophosphate linkages, disulfide linkages and restriction enzyme cleavage sites.

The support may be removed from the medium, washed free of unbound material, and then examined for the presence of extended primer copies, for example, by detecting the presence of a label or a reporter group. Generally, this examination involves contacting the support with the remaining members of a signal producing system in order to produce a signal in relation to the presence of the target nucleotide sequence in the sample.

Detection of the signal will depend upon the nature of the signal producing system utilized. If the label or reporter group is an enzyme, additional members of the signal producing system would include enzyme substrates and so forth. The product of the enzyme reaction is preferably a luminescent product, or a fluorescent or non-fluorescent dye, any of which can be detected spectrophotometrically, or a product that can be detected by other spectrometric or electrometric means. If the label is a fluorescent molecule the medium can be irradiated and the fluorescence determined. Where the label is a radioactive group, the medium can be counted to determine the radioactive count.

Various techniques can be employed for preparing a polydeoxynucleotide primer, extender probe, or other polynucleotide. They can be obtained by biological synthesis or by chemical synthesis. For short sequences (up to about 100 nucleotides) chemical synthesis will frequently be more economical as compared to the biological synthesis. In addition to economy, chemical synthesis provides a convenient way of incorporating low molecular weight compounds and/or modified bases during the synthesis step. Furthermore, chemical synthesis is very flexible in the choice of length and region of the target polynucleotide binding sequence. The polydeoxynucleotide primer and extender probe can be synthesized by standard methods such as those used in commercial automated nucleic acid synthesizers. Chemical synthesis of DNA on a suitably modified glass or resin can result in DNA covalently attached to the surface. This may offer advantages in washing and sample handling. For longer sequences standard replication methods employed in molecular biology can be used such as the use of M13 for single stranded DNA as described by J. Messing (1983) *Methods Enzymol,* 101, 20–78.

Other methods of oligonucleotide synthesis include phosphotriester and phosphodiester methods (Narang, et al. (1979) *Meth. Enzymol* 68: 90) and synthesis on a support (Beaucage, et al., (1981) *Tetrahedron Letters* 22: 1859–1862) as well as phosphoramidate technique, Caruthers, M. H., et al., "Methods in Enzymology," Vol. 154, pp. 287–314 (1988), and others described in "Synthesis and Applications of DNA and RNA," S. A. Narang, editor, Academic Press, New York, 1987, and the references contained therein.

In some instances, the 3'-end of a polynucleotide will be modified to prevent reaction with template dependent DNA polymerase or to append a binding sequence. The 3'-end can, for example, be modified by ligation of a dideoxynucleotide or a ribonucleotide followed by oxidation of the ribose with periodate followed by reductive amination of the resulting dialdehyde with borohydride and a bulky amine such as aminodextran.

The polydeoxynucleotide primer, extender probe, or other polynucleotides can be prepared by standard automated techniques.

As a matter of convenience, the reagents employed in the present invention can be provided in a kit in packaged combination with predetermined amounts of reagents for use in the present method. In assaying for a polynucleotide analyte in a sample, a kit useful in the present method can comprise, in packaged combination with other reagents, reagents for forming a target nucleotide sequence from a polynucleotide analyte, an extender probe having at its 3'-end a sequence hybridizable with a first sequence in a target nucleotide sequence and having a sequence that is homologous to a second sequence of the target nucleotide sequence, wherein the second sequence is 5' and non-contiguous with the first sequence, and a polydeoxynucleotide primer, the latter of which can be labeled or can be provided with groups to render the sequence labeled or bound to a support.

For use in a method of producing multiple copies, the kit will contain a polydeoxynucleotide primer. Either of the kits above can further include in the packaged combination deoxynucleoside triphosphates such as deoxynucleoside triphosphates, e.g., deoxyadenosine triphosphate (dATP), deoxyguanosine triphosphate (dGTP), deoxycytidine triphosphate (dCTP) and deoxythymidine triphosphate (dTTP). The kit can further include a polydeoxynucleotide polymerase and members of a signal producing system and also various buffered media, some of which may contain one or more of the above reagents.

The relative amounts of the various reagents in the kits can be varied widely to provide for concentrations of the reagents which substantially optimize the reactions that need to occur during the present method and to further substantially optimize the sensitivity of the assay. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. Each reagent can be packaged in separate containers or some reagents can be combined in one container where cross-reactivity and shelf life will permit.

EXAMPLES

The invention is demonstrated further by the following illustrative examples. Temperatures are in degrees centigrade (°C.) and parts and percentages are by weight, unless otherwise indicated.

EXAMPLE

The formation and amplification of a single stranded polydeoxynucleotide having two segments that are noncontagious and complementary with each other stem-loop molecule) was carried out using 0.1 picomole of single-stranded M13mp19 (target DNA depicted in FIG. 3, Bethesda Research Laboratories (BRL)) in a 100 microliter reaction containing 10 mM Tris-Cl, pH 8.3, 50 mM KCl, 1.5 mM $MgCl_2$, 0.01% gelatin and 200 micromolar deoxynucleotide triphosphates (dNTPs). In the presence of 1 micromolar single primer amplification (SPA) primer 2 (polydeoxynucleotide primer) and varying amounts of the extender probe 1 (1, 0.5, 0.1, 0.01, and 0.001 micromolar), the above mixture was heated to 95° C. for 5 minutes and cooled to room temperature for 15 minutes. This allows the extender probe to anneal to target DNA. Taq polymerase (Stratagens) was added (5 units) and the temperature was cycled as follows: 90° C.—30 seconds, 55° C. —60 seconds, 72° C.—90 seconds. This temperature profile was repeated 30 times. The same portion of the target molecule (less 135 bases) was amplified by PCR under identical conditions using a 1.0 micromolar concentration of primer 4. Concentrations of primer 3 were identical to those of the extender probe to allow for a direct comparison. The expected size of amplification products for SPA and PCR were 1015 and 880 base pairs, respectively. Aliquots (5 microliters) taken after 0, 10, 20, and 30 cycles from both SPA and PCR reaction mixtures were electrophoresed on a 1% agarose gel and stained with ethidium bromide. Based on the mobilities of molecular weight standards, a single band of approximately 1015 base pairs appeared following 10, 20 and 30 cycles of SPA at each concentration of the extender probe. Examination of PCR product(s) revealed a band of approximately 880 base pairs, as well as the formation of additional high molecular weight fragments with continued cycling. At the lowest concentration of primer 3, a PCR product was not detected at 10 or 20 cycles (See Table II).

Target concentration was decreased to 10 attomoles/ 100 microliter reaction and amplified using SPA or PCR. Individual reaction components, as well as time and temperature cycling parameters, were as described previously. SPA primer 2 and PCR primer 4 remained 1.0 micromolar in the presence of 0.1, 0.01 or 0.001 micromolar of the extender probe 1 or PCR primer 3. Reactions were heated to 95° C. for 5 minutes and cooled to room temperature for 30 minutes. Aliquots (5 microliters) taken after 0, 15 and 30 cycles were electophoresed on a 0.8% agarose gel and stained as descirbed. A single band of approximately 1015 base pairs appeared following 30 cycles of SPA at each concentration of extender probe. PCR reactions showed a band of approximately 880 base pairs only at the highest concentration of primer 3 (0.1 micromolar) after 30 cycles. A PCR product was not detected at lower concentrations of primer 3 following 30 temperature cycles (See Table III).

TABLE II

Comparison of SPA and PCR at 0.1 picomole of target

| Conc extender probe | Conc SPA primer | Ratio | Appearance of 1015 bp band Cycle No. | | | |
|---|---|---|---|---|---|---|
| (micromolar) | (micromolar) | 2/1 | 0 | 10 | 20 | 30 |
| 1.0 | 1.0 | 1:1 | − | + | + | + |
| 0.5 | 1.0 | 2:1 | − | + | + | + |
| 0.1 | 1.0 | 10:1 | − | + | + | + |
| 0.01 | 1.0 | 100:1 | − | + | + | + |
| 0.001 | 1.0 | 1000:1 | − | + | + | + |

| Conc PCR primer 3 | Conc PCR primer 4 | Ratio | Appearance of 880 bp band Cycle No. | | | |
|---|---|---|---|---|---|---|
| (micromolar) | (micromolar) | 4/3 | 0 | 10 | 20 | 30 |
| 1.0 | 1.0 | 1:1 | − | + | +* | +* |
| 0.5 | 1.0 | 2:1 | − | + | +* | +* |
| 0.1 | 1.0 | 10:1 | − | + | +* | +* |
| 0.01 | 1.0 | 100:1 | − | +# | + | +* |
| 0.001 | 1.0 | 1000:1 | − | + | − | + |

(*) indicates more than one band and/or a smear.
(#) indicates a very faint band observed.

TABLE III

Comparison of SPA and PCR at 0.1 attomole of target

| Conc extender probe | Conc SPA primer | Ratio | Appearance of 1015 bp band Cycle No. | | |
|---|---|---|---|---|---|
| (micromolar) | (micromolar) | 2/1 | 0 | 15 | 30 |
| 0.1 | 1.0 | 10:1 | − | − | + |
| 0.01 | 1.0 | 100:1 | − | − | + |
| 0.001 | 1.0 | 1000:1 | − | − | + |

TABLE III-continued

Comparison of SPA and PCR at 0.1 attomole of target

| Conc PCR primer 3 (micromolar) | Conc PCR primer 4 (micromolar) | Ratio 4/3 | Appearance of 880 bp band Cycle No. | | |
|---|---|---|---|---|---|
| | | | 0 | 15 | 30 |
| 0.1 | 1.0 | 10:1 | — | — | + |
| 0.01 | 1.0 | 100:1 | — | — | — |
| 0.001 | 1.0 | 1000:1 | — | — | — |

1: Extender probe (56 b): The 3' 31 bases hybridize to pos. 1702 to 1732 of the target DNA. The 5' 25 bases do not hybridize to the target.

5'-TGTTGTTCCGTTAGTTCGTTTTATTCAT-
AGTTAGCGTAACGATCTAAAGTTTTGTC-3'

2: SPA primer (25 b): This sequence is the same as pos. 744 to 768 of the target. It is also the same as the 5' 25 bases of the externder probe.

5'-TGTTGTTCCGTTAGTTCGTTTTATT-3'

3: PCR primer (31 b): This primer is the same as the 3' 31 bases of the extender probe.

5'-CATAGTTAGCGTAACGATCTAAAGTTTTGTC-3'

4: PCR primer (25 b): This sequence is the same as pos. 852 to 876 of the target.

5'-GTTGAAATTAACCATCTCAAGCCC-3'

The above discussion includes certain theories as to mechanisms involved in the present invention. These theories should not be construed to limit the present invention in any way, since it has been demonstrated that the present invention achieves the results described.

The above description and examples fully disclose the invention including preferred embodiments thereof. Modifications of the methods described that are obvious to those of ordinary skill in molecular biology and related sciences are intended to be within the scope of the following claims.

What is claimed is:

1. A method for producing a single stranded polydeoxynucleotide having two segments that are non-contiguous and complementary with each other, said method comprising the steps of:

providing in combination a polynucleotide having two non-contiguous, non-complementary nucleotide sequences S1 and S2 wherein S2 is 5' of S1 and is at least ten nucleotides long and an extender probe comprised of two deoxynucleotide sequences, wherein the sequence at the 3' end of said extender probe is hybridizable with S1 and the other of said deoxynucleotide sequences is homologous to S2 DNA polymerase and deoxynucleoside triphosphates, and extending said extender probe along said polynucleotide, thereby producing said single stranded polydeoxynucleotide.

2. The method of claim 1 which further comprises providing in said combination a polydeoxynucleotide primer capable of hybridizing at least at its 3'-end with a nucleotide sequence complementary to S2 under conditions where (a) said extended extender probe is rendered single stranded, (b) said polydeoxynucleotide primer hybridizes with and is extended along said extended extender probe to form a duplex comprising extended primer, (c) said extended primer is dissociated from said duplex, and (d) said primer hybridizes with and is extended along said extended primer to form a duplex comprising extended primer.

3. The method of claim 2 wherein steps (c) and (d) are repeated.

4. The method of claim 3 wherein the concentration of said extender probe is substantially lower than that of said polydeoxynucleotide primer.

5. The method of claim 3 wherein the concentration of said extender probe is less than one percent that of said polydeoxynucleotide primer.

6. A method for producing multiple copies of a single stranded polydeoxynucleotide having two segments that are non-contiguous and complementary with each other, said method comprising the step of:

providing in combination, either concomitantly or wholly or partially sequentially, a polynucleotide having two non-contiguous, non-complementary nucleotide sequences, S1 and S2, wherein S2 is 5' of S1 and is at least ten nucleotides long, an extender probe comprised of two deoxynucleotide sequences, wherein the sequence at the 3' end of said extender probe is hybridizable with S1 and the other of said nucleotide sequences is homologous to S2 and not complementary to said polynucleotide, a polydeoxynucleotide primer capable of hybridizing at least at its 3' end with a nucleotide sequence complementary to S2, DNA polymerase, and deoxynucleoside triphosphates under conditions where (a) said extender probe is extended along said polynucleotide to form a duplex, (b) said extended extender probe is dissociated from said duplex, (c) said polydeoxynucleotide primer hybridizes with and is extended along said extended extender probe to form a second duplex comprising extended primer (d) said extended primer is dissociated from said second duplex, and (e) said primer hybridizes with and is extended along said extended primer to form a duplex comprising extended primer, and steps (d) and (e) are repeated, thereby producing multiple copies of said single stranded polynucleotide.

7. The method of claim 6 wherein steps (d) and (e) are repeated at least three times.

8. The method of claim 6 wherein the concentration of said extender probe is less than one percent that of said polydeoxynucleotide primer.

9. The method of claim 6 wherein at least a fifteen deoxynucleotide sequence of said extender probe hybridizes with S1.

10. The method of claim 6 wherein said polydeoxynucleotide primer contains at least a fifteen deoxynucleotide sequence capable of hybridizing with a sequence complementary to S2.

11. The method of claim 6 wherein said polynucleotide is DNA.

12. A method for detecting the presence of a target nucleotide sequence in a medium suspected of containing said target nucleotide sequence, said target nucleotide sequence having two non-contiguous, non-complementary nucleotide sequences S1 and S2 wherein S2 is 5' of S1 and at least 10 nucleotides long, said method comprising the steps of:

(a) providing in combination, either concomitantly or wholly or partially sequentially, said medium, an extender probe having two deoxynucleotide sequences wherein the sequence at the 3' end of said extender probe is hybridizable with S1 and the other of said deoxynucleotide sequences is homologous to S2 and not complementary to said target nucleotide sequence, a polydeoxynucleotide primer capable of hybridizing with a nucleotide sequence complementary to S2, DNA polymerase and deoxynucleoside triphosphates under conditions wherein (i) said extender probe is extended along said polynucleotide to form a duplex, (ii) said extended extender probe is dissociated from said duplex, (iii) said primer hybridizes with and is extended along said extended extender probe to form a duplex comprising extended primer, (iv) said extended primer is dissociated from said duplex, and (v) said primer hybridizes with and is extended along said extended primer to form a duplex comprising extended primer and steps (iv) and (v) are repeated, and (b) examining for the presence of said extended primer to detect the presence of said target nucleotide sequence.

13. The method of claim 12 wherein steps (iv) and (v) are repeated at least three times.

14. The method of claim 12 wherein the concentration of said extender probe is less than one percent that of said polydeoxynucleotide primer.

15. The method of claim 12 wherein at least a fifteen nucleotide sequence of said extender probe hybridizes with S1.

16. The method of claim 12 wherein said polydeoxynucleotide primer contains at least a fifteen nucleotide sequence capable of hybridizing with a sequence complementary to S2.

17. The method of claim 12 wherein S1 and S2 each respectively contain from 10 to 100 nucleotides.

18. The method of claim 12 wherein said target nucleotide sequence is DNA.

19. The method of claim 12 wherein the concentration of said extender probe is less than 1 nM and the concentration of said polydeoxynucleotide primer is greater than 100 nM.

20. The method of claim 12 wherein said polydeoxynucleotide primer is labeled with a reporter molecule.

21. The method of claim 12 wherein said polydeoxynucleotide primer contains a nucleotide sequence other than the sequence that hybridizes with said sequence complementary to S2.

22. The method of claim 21 wherein said presence of said extended primer is detected by examining for a reporter molecule covalently bonded to a nucleotide sequence that is complementary to a portion of said target nucleotide sequence other than S1 or S2.

23. A method for detecting the presence of a polynucleotide analyte in a sample suspected of containing said polynucleotide analyte, said method comprising the steps of:

(a) treating a medium containing said sample to form a single stranded target nucleotide sequence from said polynucleotide analyte, if present, said target nucleotide sequence having two non-contiguous, non-complementary nucleotide sequences S1 and S2 wherein S2 is 5' of S1, and is at least ten nucleotides long, (b) combining said medium with an extender probe having two deoxynucleotide sequences wherein the sequence at the 3' end of said extender probe is hybridizable with S1 and the other of said deoxynucleotide sequences is homologous to S2 and not complementary to said target sequence, a polydeoxynucleotide primer capable of hybridizing with a nucleotide sequence complementary to S2, deoxynucleoside triphosphates, and DNA template dependent polydeoxynucleotide polymerase under conditions wherein (i) said extender probe is hybridized with and is extended along said target nucleotide sequence to form a duplex, (ii) said extended extender probe is dissociated from said duplex, (iii) said primer hybridizes with and is extended along said extended extender probe to form a duplex comprising extended primer, (iv) said extended primer is dissociated from said duplex, and (v) said primer hybridizes with and is extended along said extended primer to form a duplex comprising extended primer and steps (iv) and (v) are repeated, wherein steps (a) and (b) are performed concomitantly or wholly or partially sequentially, and (c) examining for the presence of said extended primer to detect the presence of said polynucleotide analyte.

24. The method of claim 23 wherein steps (iv) and (v) are repeated less than 30 times.

25. The method of claim 23 wherein the concentration of said extender probe is less than one percent that of said polydeoxynucleotide primer.

26. The method of claim 23 wherein at least a fifteen nucleotide sequence of said extender probe hybridizes with S1.

27. The method of claim 23 wherein said polydeoxynucleotide primer contains at least a fifteen nucleotide sequence capable of hybridizing with a sequence complementary to S2.

28. The method of claim 23 wherein S1 and S2 each respectively contain from 10 to 100 nucleotides.

29. The method of claim 23 wherein said polynucleotide analyte is DNA.

30. The method of claim 23 wherein said polynucleotide analyte is RNA and said medium includes reverse transcriptase.

31. The method of claim 23 wherein the concentration of said extender probe is less than 1 nM and the concentration of said polydeoxynucleotide primer is greater than 100 nM.

32. The method of claim 23 wherein said polydeoxynucleotide primer is labeled with a reporter molecule.

33. The method of claim 32 wherein step (c) includes examining for the presence of said reporter molecule covalently bonded to a nucleotide sequence complementary to a sequence present in said target nucletide sequence other than S1 and S2.

34. The method of claim 23 wherein said deoxynucleoside triphosphates are dATP, dGTP, dCTP, and dTTP.

35. The method of claim 23 wherein steps (4) and 5) are repeated such that the number of said duplexes formed is increased by at least a factor of 1000.

36. The method of claim 32 wherein said reporter molecule is selected from the group consisting of fluorescers, chemiluminescers, promotors, co-enzymes, radioactive substances, amplifiable polynucleotide sequences, small organic molecules, catalysts and polynucleotide sequences coding for catalysts.

37. The method of claim 23 wherein said polydeoxynucleotide primer is labeled with a ligand.

38. The method of claim 23 wherein said polydeoxynucleotide primer contains a nucleotide sequence other than the sequence that hybridizes with said sequence complementary to S2.

39. The method of claim 38 wherein said nucleotide sequence of said polydeoxynucleotide primer contains a sequence that, when hybridized to its complementary sequence, can be bound specifically by a receptor.

40. The method of claim 39 wherein said receptor is selected from the group consisting of repressors, activators, and nucleases.

41. The method of claim 38 wherein said nucleotide sequence of said polydeoxynucleotide primer contains a sequence that when hybridized to its complementary sequence, can be bound specifically by a receptor, and said extended primer is detected by binding said receptor to said extended primer.

42. A kit comprising in packaged combination:

an extender probe having at its 3' end a sequence hybridizable with a first sequence in a target nucleotide sequence and having a sequence that is homologous to a second sequence of said target nucleotide sequence, wherein in said target nucleotide sequence said second sequence is 5' and non-contiguous with said first sequence, a polydeoxynucleotide primer capable of hybridizing with a sequence that is complementary with said second sequence, template dependent DNA polymerase, and deoxynucleoside triphosphates.

43. The kit of claim 42 wherein the amount of said extender probe is less than one percent the amount of said polydeoxynucleotide primer.

44. The kit of claim 42 wherein said extender probe comprises a 10 to 100 nucleotide sequence hybridizable with a target nucleotide sequence.

45. The kit of claim 42 wherein said extender probe comprises a 10 to 100 nucleotide sequence that is homologous to a sequence in a target nucleotide sequence.

46. The kit of claim 42 wherein said polydeoxynucleotide primer comprises a 10 to 100 nucleotide sequence capable of hybridizing with a sequence that is complementary to said second sequence.

47. The kit of claim 42 wherein said polydeoxynucleotide primer is labeled with a reporter molecule.

48. The kit of claim 42 wherein said polydeoxynucleotide primer is labeled with a ligand.

49. The kit of claim 42 wherein said polydeoxynucleotide primer comprises a nucleotide sequence in addition to that capable of hybridizing with a sequence complementary to said second sequence.

* * * * *